United States Patent
Lin et al.

(10) Patent No.: US 10,016,166 B2
(45) Date of Patent: Jul. 10, 2018

(54) CONTACTLESS DETECTION METHOD WITH NOISE LIMINATION FOR INFORMATION OF PHYSIOLOGICAL AND PHYSICAL ACTIVITIES

(71) Applicant: NATIONAL TAIWAN UNIVERSITY OF SCIENCE AND TECHNOLOGY, Taipei (TW)

(72) Inventors: Yuan-Hsiang Lin, Taipei (TW); Yu-Chen Lin, Taipei (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 0 days.

(21) Appl. No.: 15/603,765

(22) Filed: May 24, 2017

(65) Prior Publication Data

US 2017/0340289 A1 Nov. 30, 2017

(30) Foreign Application Priority Data

May 31, 2016 (TW) .............................. 105116987 A

(51) Int. Cl.
*A61B 5/00* (2006.01)
*A61B 5/024* (2006.01)

(52) U.S. Cl.
CPC .......... *A61B 5/7207* (2013.01); *A61B 5/0077* (2013.01); *A61B 5/024* (2013.01); *A61B 5/725* (2013.01)

(58) Field of Classification Search
CPC ..... A61B 5/0077; A61B 5/024; A61B 5/0255; A61B 5/7207; A61B 5/725; A61B 6/7257; A61B 2503/10; A61B 5/1118; A61B 5/4866
See application file for complete search history.

(56) References Cited

U.S. PATENT DOCUMENTS

| | | | |
|---|---|---|---|
| 2015/0201873 A1* | 7/2015 | Wilmering | A61B 5/14551 600/324 |
| 2015/0265194 A1* | 9/2015 | Pollonini | A61B 5/14551 600/301 |

* cited by examiner

*Primary Examiner* — Edward Park
(74) *Attorney, Agent, or Firm* — Bacon & Thomas, PLLC

(57) ABSTRACT

A contactless detection method with noise elimination is applied to measuring the information of physiological and physical activities. It includes following steps: sensing a human body to generate an image by an image sensor; capturing a physiological signal from the image; tracing a feature point of the human body in the image to generate a physical activity signal; and calculating information of physical activities covering step count, speed and calories according to the physical activity signal and the physiological signal. In particular, the contactless detection method treats the physiological signal cooperated with the physical activity signal to separate a noise from the physiological signal, so as to generate an ideal physiological signal. Therefore, the physiological information is calculated more accurately according to the ideal physiological signal.

13 Claims, 12 Drawing Sheets

CONTACTLESS DETECTION METHOD WITH NOISE LIMINATION FOR INFORMATION OF PHYSIOLOGICAL AND PHYSICAL ACTIVITIES

BACKGROUND OF THE INVENTION

(1) Field of the Invention

The present invention relates to a method of eliminating motion noise in a physiological signal, particularly, to a contactless detection method with eliminating noise applied to measuring information of physiological and physical activities.

(2) Description of the Prior Art

With respect to monitoring physiological information during physical exercise, the contact-type conductive media is generally used in sports equipment for capturing ECG signal (Electrocardiography, ECG). With the rapid development of wear-style devices in recent years, the new products related such as wear-style heart rhythm/rate straps, watches, bracelets and the like are introduced continuously to replace obsolete ones so that the new wear-style products facilitate the users more easily understand the physiological fluctuation of their own during physical exercises.

In addition to the monitoring of the heart rhythm/rate, the majority of wear-style products also combine the accelerometer and other sensors to additionally monitor related step count, jogging speed, calorie consumption in body heat and other physical activity information. At present, the measurement of the physical activity information is normally performed through reading and analyzing related information for the step count and jogging speed from the accelerometer in these wear-style products.

However, these wear-style products are designed to be used in detection method as they must be worn on the body to contact with the body for measurement. Wearing these wear-style products in long-term may cause physical discomfort or skin malignant effects such as allergies and so on. Moreover, most people still prefer to wear redundant sundries as less as possible during exercise. Therefore, contactless product and method for detecting physiological and physical signal are naturally emerged to meet the marketing demand.

The application of obtaining images via contactless physiological signal detecting products and methods can provide a comfortable measurement environment to the user. But contactless signals are often susceptibly affected by external environmental noise seriously such as light sources, movements and so on. Additionally, in the strenuous exercise, the information of heart rhythm/rate and other physiological signals obtained from current contactless detection method will be inaccurate due to human movement. In order to improve the quality of contactless physiological signals under strenuous exercise, more effective methods are urgently needed to reduce the noises in physiological signals.

Moreover, the contactless detection method has not been effectively applied to the measurement in physical activity information. Currently, in measurement of exerciser step count or jogging-speed, the exerciser is still needed to wear the sensor generally. If both of the physiological signal noise being ably reduced and the measurement in physical activity information being effectively applied, the application field of contactless detection method will be effectively developed.

SUMMARY OF THE INVENTION

The object of the present invention is to provide a contactless detection method for information of physiological and physical activities with functions in eliminating the noise of the physiological signal and monitoring the information of physical activity.

In order to achieve the object aforesaid, the present invention provides a contactless detection method with noise elimination for information of physiological and physical activities, comprising steps of: providing an image sensor for capturing an image of a human body portion to produce a primitive image such as a face image; defining a feature point of the human body portion from the primitive image; tracing an information for coordinate movement of the feature point to create a displacement signal; capturing a complexion fluctuation of the human body portion to form a pending physiological signal including a noise; inputting the displacement signal and the pending physiological signal into an adaptive filter such as a single stage adaptive filter or a cascade adaptive filter to eliminate the noise in the pending physiological signal for generating an ideal physiological signal; performing a first peak/trough detection on the ideal physiological signal to calculate out an physiological information including pulse rate and exercise intensity; and performing a second peak/trough detection on the displacement signal to calculate out an information of physical activity such as step count, jogging speed, calorie consumption, exercise duration and distance, etc.

In an embodiment, said method further comprises: defining a region of interest for the human body portion in the primitive image; and updating the coordinate of the region of interest dynamically in accordance with the displacement signal while the region of interest moving with the human body portion.

In an embodiment, said pending physiological signal is a pending heart rhythm signal, the ideal physiological signal is an ideal heart rhythm signal, and the physiological information is a value of heart rhythm, the method further comprises: extracting a green channel signal, a red channel signal and a blue channel signal from the region of interest; and performing a color space linear combination algorithm such as green-red difference, and chrominance based algorithm on the green channel signal, the red channel signal, and the blue channel signal prior to inputting the pending heart rhythm signal to the adaptive filter.

In an embodiment, said method further comprises: locking a relative positional relationship between the feature point and the region of interest for defining the feature point and the region of interest.

In an embodiment, said method further comprises: tracing information for coordinate movement of a center point in the region of interest for replacing the information for the coordinate movement of the feature point to create another displacement signal.

In an embodiment, said method further comprises: performing a band pass filtering or temporal normalization on the ideal heart rhythm signal prior to performing the first peak/trough detection; and performing another band pass filtering and a direct-current subtraction on the displacement signal to generate a pre-processed displacement signal prior to performing the second peak/trough detection.

In an embodiment, the procedure of generating the ideal heart rhythm signal comprising: taking the displacement signal as a reference offset source signal for the adaptive filter; offering a filter coefficient for operation with the reference offset source signal to obtain an hypothetical noise approaching the noise; and performing a SUM logical operation on both of the hypothetical noise and the pending heart rhythm signal to obtain the ideal heart rhythm signal.

In an embodiment, said method further comprises: providing a peak/trough detection algorithm; judging whether or not the pre-processed displacement signal has an amplitude below a threshold value; and if the amplitude of the pre-processed displacement signal is below the threshold value, a corresponding pulse rate is detected with the peak/trough detection algorithm from a time domain waveform of the ideal heart rhythm signal; otherwise, an instant pulse rate is measured by detecting a maximum occurrence within a normal heartbeat range in a frequency domain spectrum of the ideal heart rhythm signal.

In an embodiment, said method further comprises: providing a first judging mechanism comprising steps of: judging the human body portion is in active condition or at rest condition; if the human body portion is judged as in active condition, the pending physiological signal and the pre-processed displacement signal will be input into the adaptive filter for being treated by a signal mixing process to eliminate the noise; and if the human body portion is judged as at rest condition, the pending physiological signal will or will not be input into the adaptive filter for being treated by the signal mixing process so that the pending physiological signal is directly used to calculate the physiological information; and providing a second judging mechanism for determining whether or not the pre-processed displacement signal of the feature point needs to be mixed with the pending physiological signal in the signal mixing process before calculating the information of physical activity by using the pre-processed displacement signal.

The exemplary embodiment of the foregoing method is possible to simultaneously monitor both of the physiological state and physical activity state by providing only an image sensor and a contactless signal processing system. Moreover, the method can accurately measure the heart rhythm value with elimination of the motion noise even in the case of human movement, which means that it can solve the pending problem for inaccuracy in contactless detection of heart rhythm signal, which is incurred by the heart rhythm signal being susceptible to movement of the user's face.

DESCRIPTION OF THE PREFERRED EMBODIMENTS

Regarding technical contents, features and effects disclosed above and other technical contents, features and effects of the present invention will be clearly presented and manifested in the following detailed description of the exemplary preferred embodiments with reference to the accompanying drawings which form a part hereof. It is to be understood that other embodiments may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," and "coupled," and variations thereof herein are used broadly and encompass direct and indirect connections, couplings, and mountings.

Figure 1:
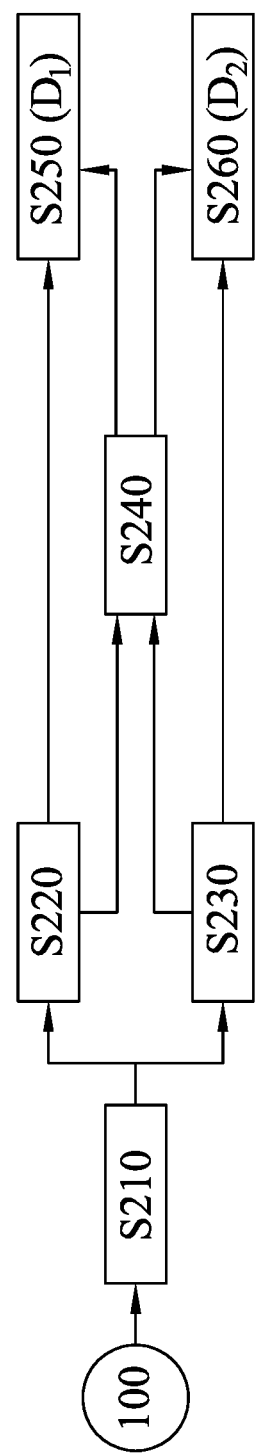
FIG. 1 is a schematic view illustrating an overall systematic invention concept via a block flowchart for a contactless detection method with noise elimination for information of physiological and physical activities in an exemplary embodiment of the present invention.
Figure 2A:
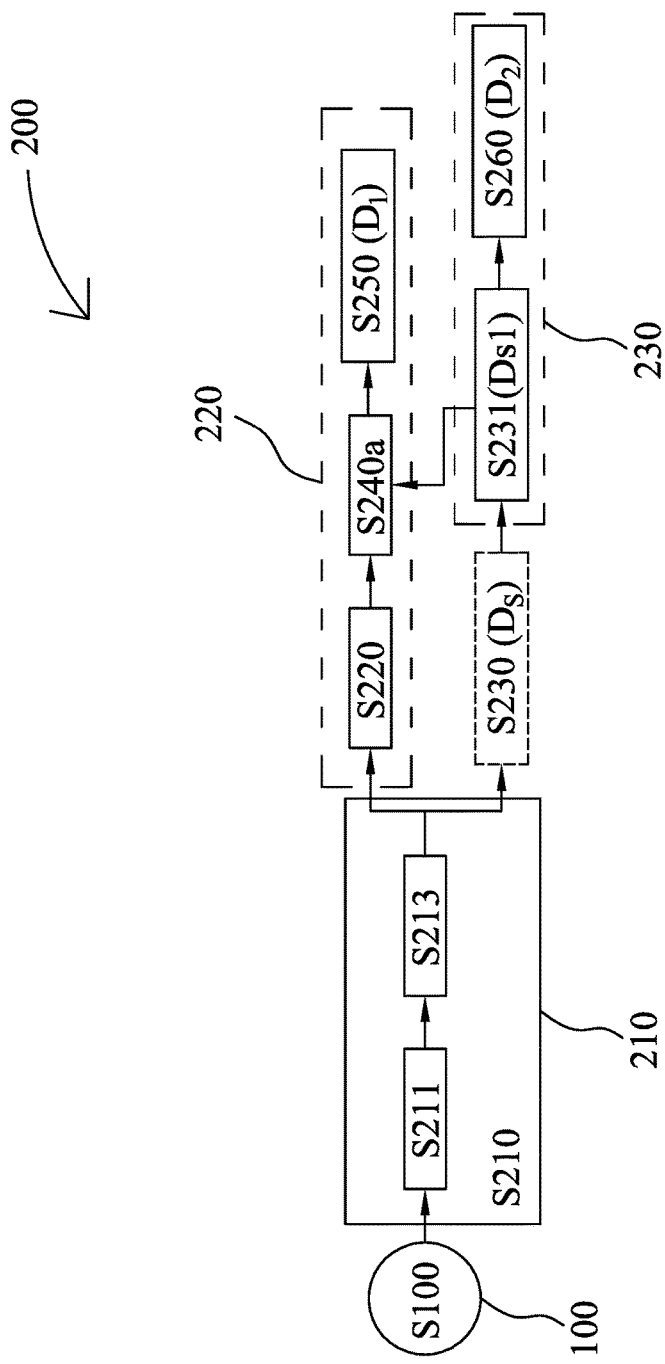
FIG. 2A is a schematic view showing a contactless detection system and a signal processing flow thereof for detecting the information of physiological and physical activities in an exemplary embodiment of the present invention.

FIG. 1 is a schematic view illustrating an overall systematic invention concept via a block flowchart for a contactless detection method with noise elimination for information of physiological and physical activities in an exemplary embodiment of the present invention. In one embodiment, the contactless detection method can be performed by an image sensor 100 cooperating with a contactless signal processing system 200, as shown in FIG. 2A. The image sensor 100 such as a webcam or a light sensing component generates a primitive image such as a face image by sensing a human body portion. Subsequently, the primitive image is treated by performing an image processing process in step S210 for extracting a pending physiological signal in step S220 and extracting a physical activity signal in step S230. The pending physiological signal is mixed with the physical activity signal in step S240, to eliminate noise in the pending physiological signal for forming a physiological information $D_1$ in step S250 and forming an information $D_2$ of physical activity in step S260. Specifically, the present invention features that the pending physiological signal and the physical activity signal are all originated from the primitive image via the image sensor 100, and the physical activity signal is not only used to compute the information $D_2$ of physical activity but also involved in the noise elimination process of the pending physiological signal.

FIG. 2A is a schematic view showing a contactless detection system and a signal processing flow thereof for information of physiological and physical activities in an exemplary embodiment of the present invention, which illustrates the first image sensing process and initial signal process. Here, the pending physiological signal retrieved from the primitive image from previous image sensor 100 is, for example, a pending heart rhythm signal containing a motion noise. The extracted physical activity signal is a displacement signal Ds of a feature point of a human body portion. The physiological information $D_1$ is, for example, a heart rhythm value. The information $D_2$ of physical activity is, for example, number count of steps, jogging speed, or calorie number of heat consumption in human body. Noticeably, the displacement signal Ds of the feature point is used in two cases as firstly, it is used for the pending heart rhythm signal to be processed in a noise elimination process as step S240a, which is derived from the concept of the mixing process as step S240 in FIG. 1; and secondly, it is used for calculating the information $D_2$ of physical activity in step S260.

In the embodiment of FIG. 2A, a sequence of continuous face images are captured by the image sensor 100 via image acquisition process in step S100, and then they are relayed to the image processing unit 210 to perform the image processing process as step S210. The image processing process includes detecting a face area and a region of interest (referred to ROI below) located in the face area as step S211 for measuring the heart rhythm signal by the ROI, and tracing the position change of a feature point of face to update the coordinate for the ROI thereof as step S213. The displacement signal Ds for the coordinate of the feature point of the face is generated by step S230, which is included in the concept of extracting the physical activity signal as step S230 in FIG. 1. Following steps S100 and S210, a subsequent signal processing flow are carried out by the contactless signal processing system 200. The subsequent signal processing flow includes steps S220, S240a and S250 for processing the heart rhythm signal by a heart rhythm detecting module 220, as well as includes steps S231 and S260 for processing the physical activity signal by a physical activity signal processing unit 230.

More specifically speaking, within the image processing unit 210, a face detection algorithm is applied to detect a face area of a user in step S211, the face area such as eye(s), nose, mouth, and the like. Once each image is read by the image processing unit 210, a specific range in the face area is selected for detecting and tracing the coordinate of the feature point as the step S213 to update the position of the ROI. The traced information is used to create the displacement signal Ds in the step S230, namely the physical activity signal, and undergo the signal processing in step S231 to produce a pre-processed displacement signal (Ds1). During the motion of the human body, the heart rhythm measurement module 220 selects an ROI from the face area for extracting the Photoplethysmogram (referred to PPG below), namely recording the fluctuation in light or complexion in the ROI as a heart rhythm signal in step S220. Then both of the heart rhythm signal and the pre-processed displacement signal Ds1 are subjected to the noise elimination process as the step S240a, which is derived from the concept of the mixing process as the step S240 in FIG. 1, to cancel the noise in the heart rhythm signal.

Figure 2B:
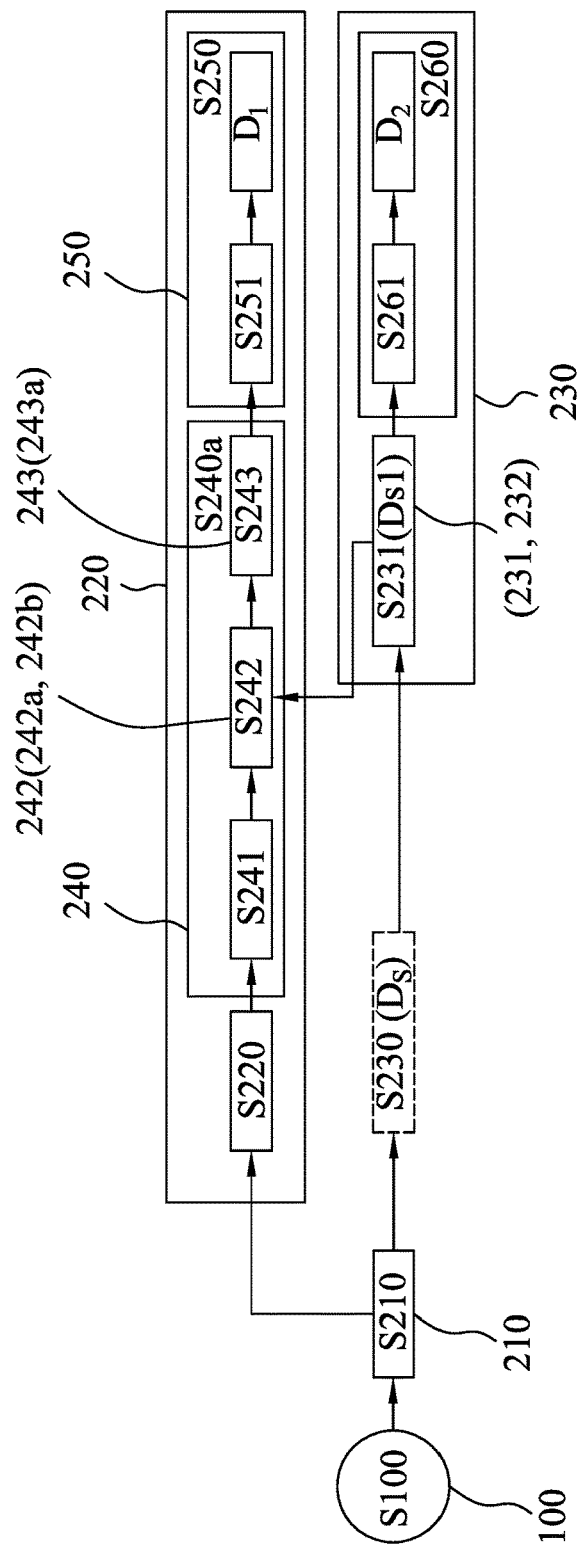
FIG. 2B is a schematic view showing the contactless detection method with noise elimination for detecting the information of heart rhythm and physical activities in an exemplary embodiment of the present invention.

FIG. 2B is a schematic view showing the contactless detection method with noise elimination for information of heart rhythm and physical activities in an exemplary embodiment of the present invention, wherein the signal flow is divided into two branches such that one upper branch depicts signal flow of the heart rhythm signal while another lower branch describes signal flow of physical activity. For the upper branch signal flow in the FIG. 2B, the heart rhythm measurement module 220 comprises a heart rhythm signal processing unit 240 and a heart rhythm calculation unit 250. The heart rhythm signal processing unit 240 includes an adaptive filter 242, and a band pass filter 243 or a temporal normalization unit 243a. The adaptive filter 242 is, for example, a single stage adaptive filter 242a shown in FIG. 5B or a cascade adaptive filter 242b shown in FIG. 5C, so the adaptive filtering process as the step S242 may be a single stage adaptive filtering process or a cascade adaptive filtering process. In order to eliminate the motion noise in the heart rhythm signal, the noise eliminating process as the step S240a of the physiological signal may involve three sub-processes that are RGB color space linear combination algorithm (referred to rPPG below) or green-red difference algorithm in the step S241, adaptive filtering process in the step S242, and band pass filtering or temporal normalization in the step S243, to enhance a signal-to-noise ratio (S/N ratio) on an ideal heart rhythm signal generated from the step S242. In the adaptive filter 242, the heart rhythm signal after the RGB color space linear combination algorithm calculating as the step S241 is subjected to the adaptive filtering process as the step S242 with the pre-processed displacement signal Ds1. The output of adaptive filtered heart rhythm signal is passed through the band pass filter 243 or the temporal normalization unit 243a, and then is input into the final heart rhythm unit 250. The final heart rhythm unit 250 calculates the heart rhythm value in the step S250 with a peak/trough detection algorithm S251 or Fast-Fourier-Transform (FFT) as step S252.

Depending on the amplitude of pre-processed displacement signal Ds1, the accuracy of the contactless detection method of the present invention can be enhanced by applying both time domain peak/trough detection and frequency domain analysis to determine an instant pulse rate. Firstly, the method of the present invention provides a peak/trough detection algorithm, and judges whether or not the pre-processed displacement signal Ds1 has an amplitude below a threshold value. If the amplitude of the pre-processed displacement signal Ds1 is below a threshold value, a corresponding pulse rate is detected with the peak/trough detection algorithm from a time domain waveform of the ideal heart rhythm signal; otherwise, the instant pulse rate can be measured by detecting the maximum occurrence of a pulse rate within a normal heartbeat range in a frequency domain spectrum of the ideal heart rhythm signal.

For the lower branch signal flow in the FIG. 2B, the physical activity signal processing unit 230 also includes a band pass filter 231 and a direct-current subtraction unit 232. The displacement signal Ds passes through the band pass filter 231 for the band pass filtering process and through the direct-current subtraction unit 232 to subtract the direct-current component of the displacement signal Ds in the step S231 to output a pre-processed displacement signal Ds1. The pre-processed displacement signal Ds1 is then subjected to a peak/trough detection step S261 to calculate the information $D_2$ of physical activity.

All the processing steps for the exemplary embodiment of the present invention will be described in more detail below.

Step S100 includes image input and camera exposure correction. Since the image produced from the contactless method by the image sensor 100 is susceptible to the fluctuation in the light, some corrections such as exposure, focal length and the like must be performed before the image acquisition process of step S100 so that a primitive image of desire is captured here.

Figure 3:
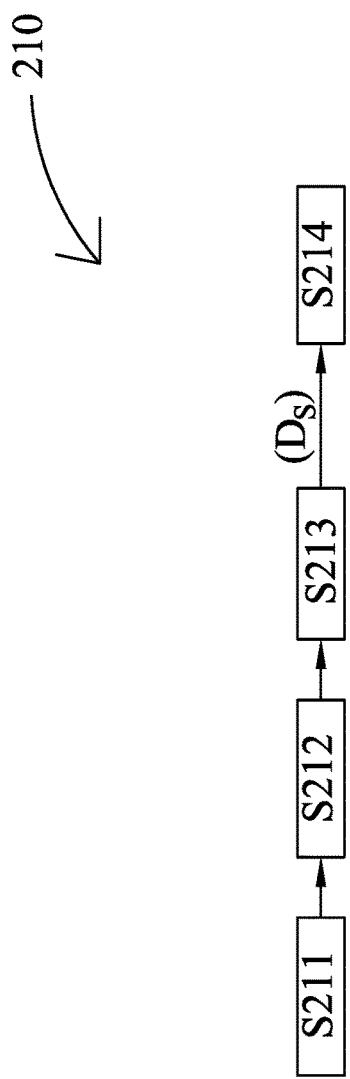
FIG. 3 is a schematic view showing an image processing flowchart in an exemplary embodiment of the present invention.

Step S210 is an initial image processing process for the primitive image from the image sensor 100 to successively undertake following sub-processes of face detection, detection and tracing the feature point and the ROI as further detailed description below. FIG. 3 is a schematic view showing an image processing flowchart for the block of 210 in FIGS. 2A and 2B. As shown in FIGS. 2A and 2B, after the previous image acquisition process (S100), the image processing process (S210) inside the image processing unit 210 comprises a sub-process (S211) for detecting the face; a sub-process (S212) for detecting and defining the feature point of the face and defining the ROI in the primitive image such that the feature point may be a point outside the measurement ROI in the face block; and a sub-process (S213) for tracing the feature point of the face to fix the ROI at a certain position of the face such as cheeks, nose or forehead. Specifically, the relative positional relationship between the ROI and the feature point is locked so that the relative positional relationship does not change with the motion of the face or human body portion. Therefore, the coordinate of the ROI during the motion of the face or human body portion can be traced by tracing the feature point of the face, and dynamically updated in sub-process (S214) in accordance with the displacement signal Ds of the feature point and said relative positional relationship.

Moreover, during movement of the human body portion or physical activity, the tracing and defining sub-process (S213) can not only record the coordinate information of the feature point such as a Y-axis movement or X-axis movement of the feature point to form a displacement signal Ds, but also trace the information in coordinate movement for the center point of the ROI to replace the coordinate information of the feature point to form another displacement signal Ds with different contents.

Figure 4C:
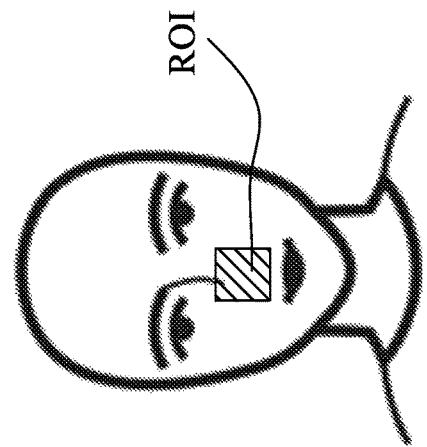
FIGS. 4A to 4C are schematic views showing various regions of interest (ROIs) in the processed face images in an exemplary embodiment of the present invention.
Figure 4B:
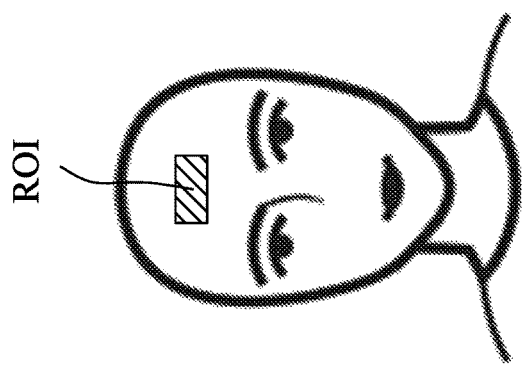
Figure 4A:
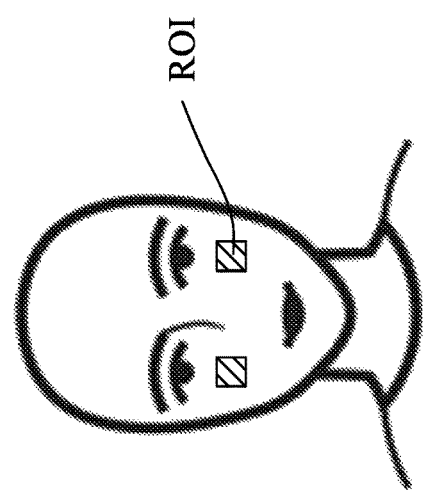

The processed results in the image processing process (S210) are shown in FIGS. 4A to 4C, which show various ROIs for the exemplary embodiment of the present invention, wherein the ROIs are defined at both cheeks in FIG. 4A, and the ROI is defined at forehead in FIG. 4B, while the ROI is defined at philtrum in FIG. 4C. As shown in FIGS. 4A to 4C, owing to human face tends to vibrate or shake with the movement of the body portion, if the adoption of the ROI is selected at forehead in FIG. 4B or at the region from the nose to the philtrum in FIG. 4C, then the heart rhythm signal obtained will be less affected by the noise.

Step S220 is a preliminary signal process for the physiological signal via capturing and editing preliminary heart rhythm signal. The preliminary heart rhythm signal is obtained by averaging following photoplethysmogram (PPG) for triple fundamental colors of red channel signal R(t), green channel signal G(t) and blue channel signal B(t) extracted from the ROI and calculated by the following formulas (1), (2), and (3). All the extracted signals are undergone the normalization process expressed as the formula (4). μ is the mean operator.

$$R(t) = \frac{\sum_{x,y \in ROI} R(x, y, t)}{|ROI|} \quad (1)$$

$$G(t) = \frac{\sum_{x,y \in ROI} G(x, y, t)}{|ROI|} \quad (2)$$

$$B(t) = \frac{\sum_{x,y \in ROI} B(x, y, t)}{|ROI|} \quad (3)$$

$$C_n(t) = \frac{C(t)}{\mu(C(t))}, C \in R, G, B \quad (4)$$

Step S240a is a signal mixing process to eliminate the noise in the physiological signal. Please refer to FIG. 5, which is a measurement processing flowchart of the physiological signal. The step S240a is further decomposed a color space linear combination algorithm (S241) and a cascade adaptive filtering algorithm (S242).

Figure 5:
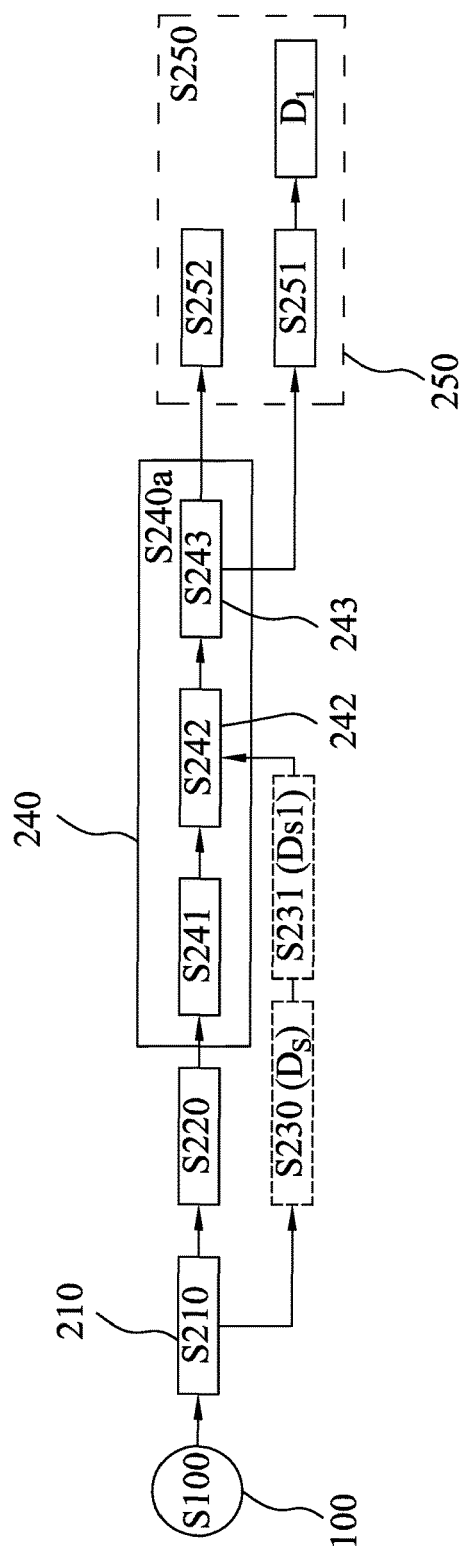
FIG. 5 is a schematic view showing a measurement processing flowchart of the physiological information in an exemplary embodiment of the present invention.
Figure 5A:
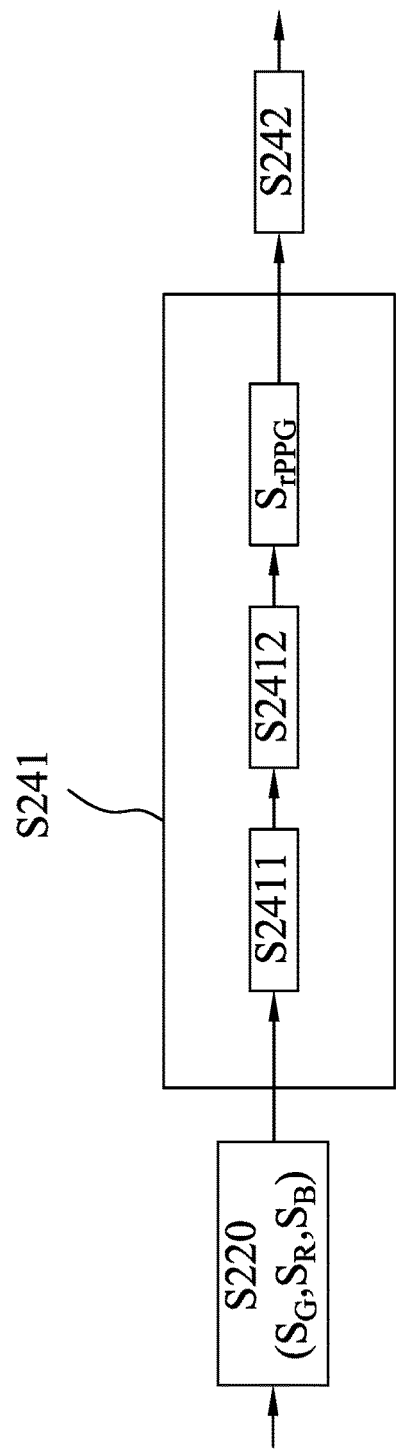
FIG. 5A is a schematic view showing a partial flowchart of a color space linear algorithm in an exemplary embodiment of the present invention.

FIG. 5A is a schematic view for a partial flowchart of the FIG. 5 in showing one of the rPPG algorithm for an exemplary embodiment of the present invention, wherein the processing block of S241 in FIG. 2B or FIG. 5 is further decomposed to sub-processing blocks S2411, S2412 to calculate the heart rhythm signal $S_{rPPG}$. Firstly, a red channel signal $R_n(t)$, a green channel signal $G_n(t)$ and a blue channel signal $B_n(t)$ are retrieved from the ROI of previous processing step S220 for form a pending physiological signal to be input into the cascade adaptive filter in step S242. Secondly, before the pending physiological signal being input into the cascade adaptive filter, the red channel signal $R_n(t)$, the green channel signal $G_n(t)$ and the blue channel signal MO are input into initial sub-process (S2411) to perform an estimation of light reflective index as shown in formulas (5) and (6). Thirdly, the red channel signal $R_n(t)$, the green channel signal $G_n(t)$, and the blue channel signal $B_n(t)$ are selected to perform a band pass filtering process (S2412) to generate the intermediate signals of ($I_{Rf}(t)$, $I_{Gf}(t)$, $I_{Bf}(t)$). Finally, as shown in equation 7, all signals ($I_{Rf}(t)$, $I_{Gf}(t)$, $I_{Bf}(t)$) are used in one of the RGB color space linear combination methods named CHROM algorithm to calculate out a temporary heart rhythm signal $S_{rPPG}$, whose partial motion noise has been eliminated here, but it still contains some motion noise. In real practice, the triple fundamental color signals of $R_n(t)$, $G_n(t)$, and $B_n(t)$ can be obtained via referring to previous formulas (1), (2), (3) and (4).

$$X_s = 3R_n(t) - 2G_n(t) \quad (5)$$
$$Y_s = 1.5R_n(t) + G_n(t) - 1.5B_n(t)$$

$$\alpha = \frac{\sigma(X_f)}{\sigma(Y_f)} \quad (6)$$

$$S_{rPPG}(t) = 3\left(1 - \frac{\alpha}{2}\right)I_{Rf}(t) - 2\left(1 + \frac{\alpha}{2}\right)I_{Gf}(t) + 3\left(\frac{\alpha}{2}\right)I_{Bf}(t) \quad (7)$$

Where, $X_s$ and $Y_s$ denote two orthogonal chrominance signal registered from RGB three color channels;

$X_f$ and $Y_f$ are the filtered version of $X_s$ and $Y_s$ after performing the band pass filtering process (S2412), respectively; and σ denotes the standard deviation operator of the signal.

Figure 5B:
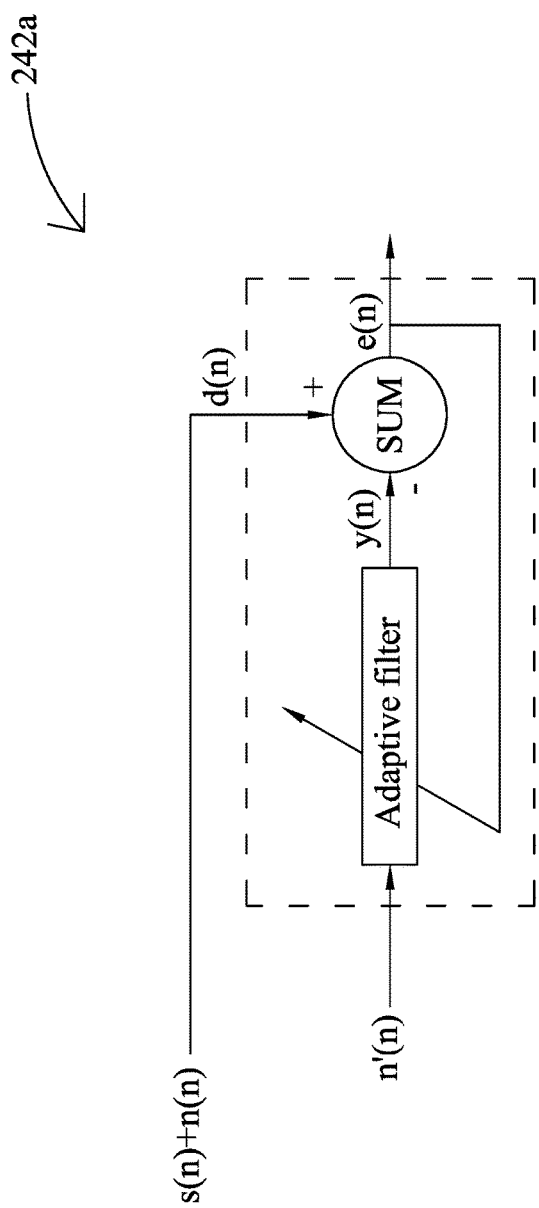
FIG. 5B is a schematic view showing a partial flowchart of an adaptive filter structure in an exemplary embodiment of the present invention.
Figure 5C:
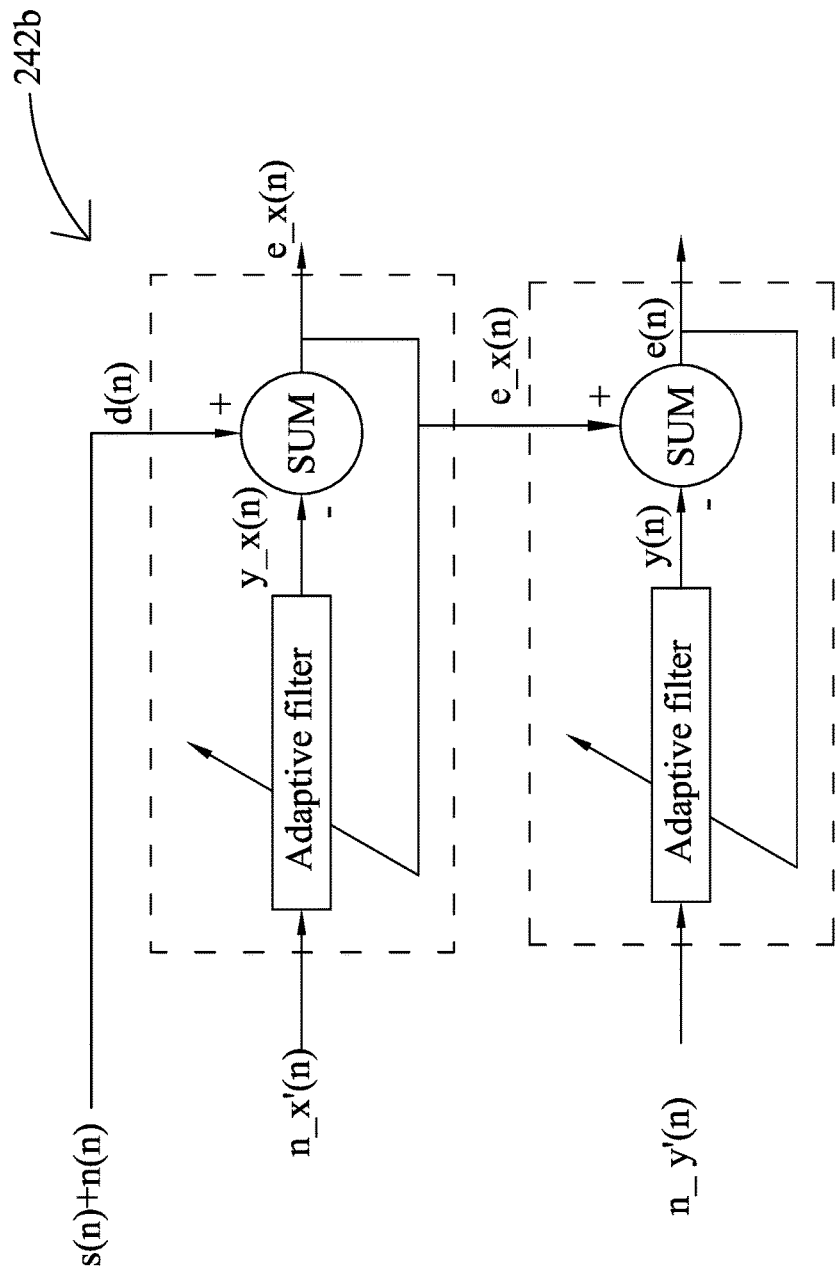
FIG. 5C is a schematic view showing a partial flowchart of a cascade adaptive filter structure in an exemplary embodiment of the present invention.

FIG. 5B and FIG. 5C are the schematic views for a partial flowchart of the FIG. 5 in showing the single stage adaptive filter and the cascade adaptive filter structures for an exemplary embodiment of the present invention, wherein the adaptive filter 242 in FIGS. 2B and 5 is processed by a SUM operator with all involving signals related. The temporary heart rhythm signal $S_{rPPG}$ obtained from previous rPPG algorithm (S241) still contains a large amount of motion noise so that both of the displacement signal Ds of the feature point and the temporary heart rhythm signal $S_{rPPG}$ are input into the adaptive filter 242 here to eliminate the noise therein to produce the ideal heart rhythm signal, which means that the large number of motion noise contained in the temporary heart rhythm signal $S_{rPPG}$ is filtered by the adaptive filtering process (S242). Using the displacement signal Ds of the feature point to adapt the temporary heart rhythm signal $S_{rPPG}$ from previous process is characterized for real-time noise elimination suitably.

As shown in FIG. 5B, there are two main channel signals involved in the single stage adaptive filter 242a as below. One channel signal is a composite signal [d(n)], which is a combinational signal of expected target signal [s(n)] with noise [n(n)] to be separated. Another channel signal is a reference offset source signal [n'(n)]), which is usually regarded as a source of pure noise used to filter out the noise [n(n)] of composite signal [d(n)]. But the actual situation is that the reference offset source signal [n'(n)] is not exactly the same as the noise [n(n)] in the composite signal [d(n)]. Therefore, the single stage adaptive filter 242a computes the reference offset source signal [n'(n)] by the filter coefficients for predicting a signal [y(n)] closer to the true noise for generating an ideal heart rhythm signal [e(n)], which is also represents a heart rhythm signal without noise.

As shown in FIG. 5C, the cascade adaptive filter 242b is formed by connecting two single stage adaptive filters in series. There are three main channel signals involved in the cascade adaptive filter 242b as below. One channel signal is a composite signal [d(n)], which is a combinational signal of expected target signal [s(n)] with noise [n(n)] to be separated. The other two channel signals are the reference offset source signals [n_x'(n)] and [n_y'(n)], which are respectively regarded as a source of referenced noise for X-direction motion, and another source of referenced noise for Y-direction motion, for filtering out the noise [n(n)] of the composite signal [d(n)]. But the actual situation is that the reference offset source signals [n_x'(n)] and [n_y'(n)] are not exactly the same as the noise [n(n)] in the composite signal [d(n)]. Therefore, the cascade adaptive filter 242b computes the reference offset source signals [n_x'(n)] and [n_y'(n)] by the filter coefficients for predicting the signals [y_x(n)] and [y(n)] closer to the true noise for generating an ideal heart rhythm signal [e(n)], which is also represents a heart rhythm signal with limited noise.

Therefore, in the embodiment of FIG. 5B, the pre-processed displacement signal Ds1 for the coordinate of the feature point or for the coordinate of the center point of the ROI is adopted for inputting into the adaptive filter 242 as the reference offset source signals [n'(n)]. In the embodiment of FIG. 5C, the pre-processed displacement signal Ds1 is decomposed into the reference offset source signals [n_x'(n)] and [n_y'(n)] in FIG. 5C. Moreover, a composite signal [d(n)] of expected target signal [s(n)] with noise [n(n)], which is equivalent to the temporary heart rhythm signal $S_{rPPG}$ output from successive rPPG algorithm (S241). A SUM logical operation is performed according to the temporary heart rhythm signal $S_{rPPG}$ and the signal [y_x(n)] and [y(n)] closer to the true noise by the adaptive filter 242, to eliminate the noise in the temporary heart rhythm signal $S_{rPPG}$ and get the ideal heart rhythm signal [e(n)], which is closer to the real heart rhythm signal.

Comparing to the temporary heart rhythm signal $S_{rPPG}$ output from previous rPPG algorithm (S241), the result of the present adaptive filtering process (S242) reflects the ideal heart rhythm signal [e(n)] generated here is closer to the real heart rhythm signal, which is not subject to noise interference. The operation formulas (8) to (10) related to the single stage adaptive filter 242a are expressed as below:

$$y(n) = \sum_{k=0}^{N-1} W_k(n) \cdot x(n-k) \tag{8}$$

$$e(n) = d(n) - y(n) \tag{9}$$

$$W_k(n+1) = W_k(n) + 2\beta e(n)x(n-k), k = 0, 1, \ldots N-1 \tag{10}$$

Where,

[x(n)] denotes an input noise [n'(n)];

[y(n)] denotes a predicting signal, which is closer to the true noise;

[e(n)] denotes an ideal signal, which is closer to the noiseless;

[d(n)] denotes composite signal of expected target signal [s(n)] with noise [n(n)];

[Wk] denotes filtering index of the adaptive filter;

[β] denotes convergence factor.

Noticeably, according to the inventive concept shown in FIG. 1, the exemplary embodiment can also provide a judging mechanism for processing the pending physiological signal in accordance with the motion status of the human body portion as follows: judging the human body portion is in active condition or at rest condition; if the human body portion is judged as in active condition, the pending physiological signal and the pre-processed displacement signal Ds1 will be input into the adaptive filter 242 for being treated by the signal mixing process (S240) to eliminate noise therein; if the human body portion is judged as at rest condition, the pending physiological signal will not be input into the adaptive filter 242 for being treated by the signal mixing process (S240) so that it is directly used to calculate the physiological information.

Step S250 is computing out the physiological information D1, referring to the FIG. 5. The heart rhythm calculation unit 250 performs different heart rhythm calculating modes based on the quality of the receiving ideal heart rhythm signal [e(n)] generated from previous adaptive filter 242 after previous adaptive filtering process (S242) having been performed. In an embodiment, the ideal heart rhythm signal [e(n)] generated from the adaptive filter 242 needs to be further processed by a band pass filtering process (S243) with exemplary cutoff frequency thereof in range of 0.8 to 3.4 Hz or a temporal normalization as expressed in formula (11), so as to improve the accuracy of subsequent process (S251) for real-time crest or trough detection before computing the physiological information $D_1$.

$$E_N(t) = \frac{e(n) - \mu(e(n))}{\sigma(e(n))} \tag{11}$$

Where,

[e(n)] denotes an output signal from the adaptive filter;

[μ] denotes the mean operator;

[σ] denotes the standard deviation operator;

In another embodiment, the physiological information $D_1$ is directly calculated out in subsequent process (S252) by converting time domain waveform of the ideal heart rhythm signal [e(n)] to frequency domain waveform by a Fast Fourier Transform (FFT).

Figure 6:
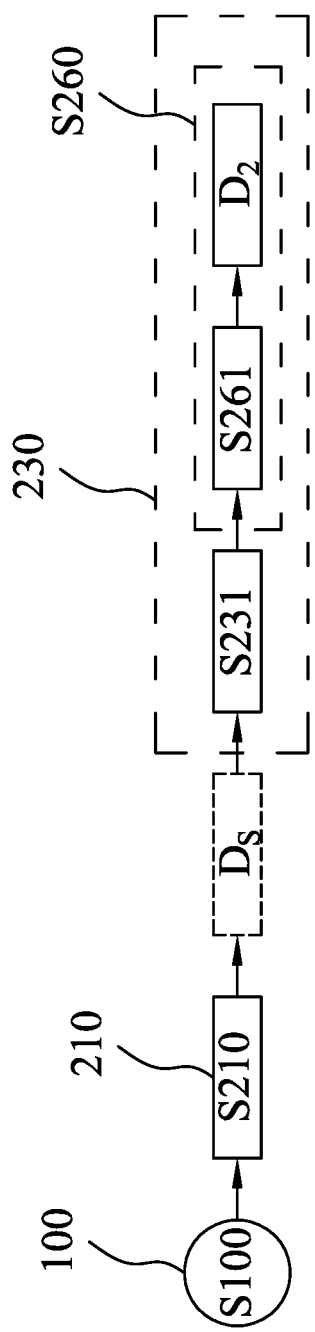
FIG. 6 is a schematic view showing a measurement processing flowchart for the information of physical activities in an exemplary embodiment of the present invention.

FIG. 6 is a schematic view showing that a partial process of the contactless detection method of the present invention is applied to measuring the information of physical activity, wherein the physical activity signal processing unit 230 is used to execute the sub-processes of S231 and S260. The partial process for detecting the information of physical activity shares the same image processing unit 210 and image processing step S210 with the process for detecting the physiological information, to obtain the displacement signal Ds of face feature point or the displacement signal Ds of the central point of the ROI. By means of the displacement signal Ds, the information $D_2$ of physical activity such as step count, jogging speed can be judged. The consumed calories for the body heat of the exerciser can be further found via both of the physiological information $D_1$ and the information $D_2$ of physical activity to serve as a reference in the movement.

Figure 7:
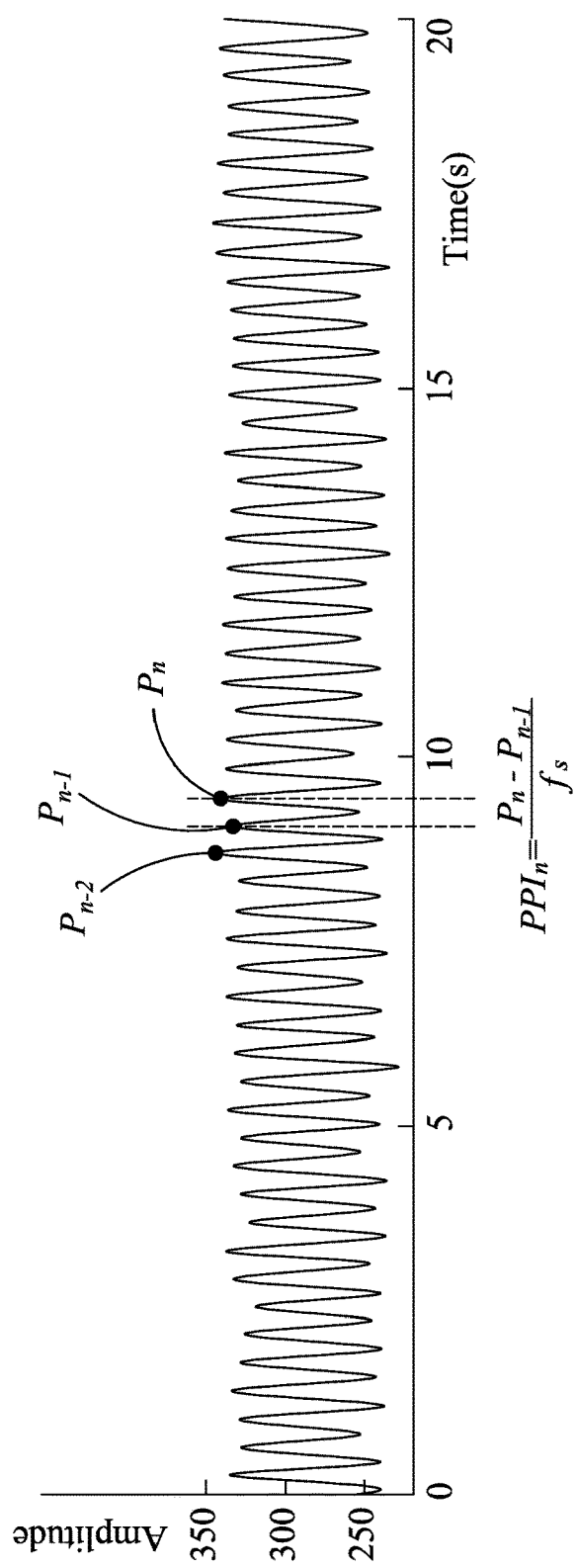
FIG. 7 shows the fluctuation for the Y-axis displacement of the feature point captured as a user during exercising in an exemplary embodiment of the present invention.

FIG. 7 shows the fluctuation for the Y-axis displacement of the feature point captured as a user during exercising in an exemplary embodiment of the present invention. The Y-axis displacement of the feature point or the center point of the ROI can be recorded by means of tracing the feature point in the processing step S213 or the center point of the ROI. The recorded signal as FIG. 7 will fluctuate with the number of steps. We can find that the generation of each crest is in synchronization with fluctuation for the number of steps so that the step count can be calculated by means of crest detection. The processing flow of the physical activity signal is described in more detail with following sub-processing step S231 and step S260.

Step S231: In order to perform the subsequent peak/trough detection process (S261) for the displacement signal Ds, the displacement signal Ds can be firstly filtered through the low pass filter or the band pass filter to filter out high frequency signal and to subtract the direct-current component of the displacement signal Ds if the quality of the displacement signal Ds is not good.

Step S260: The calculation of the step count is performed by the algorithm for the peak/trough detection process (S261). In addition to foregoing functions for calculation of the step count, the speed of movement as shown in the formulas (12) and (13) can also be computed via detection every time point for each wave crest or trough as shown in FIG. 7 with following formulae.

$$PPI_n = \frac{P_n - P_{n-1}}{fs} \quad (12)$$

$$Velocity_n = \frac{Step\ length}{PPI_n} \times 3.6\ (km/hr) \quad (13)$$

Where, $PPI_n$ denotes the time difference between adjacent wave crests, specifically for the current wave crest to the previous adjacent wave crest;

$P_n$ denotes the current wave crest;

$P_{n-1}$ denotes the previous adjacent wave crest;

$f_s$ denotes the image updating frequency in accordance with the camera capture frequency;

Step length denotes the length of averaged step in meter unit;

$Velocity_n$ denotes estimated instantaneous jogging speed.

The determining factors for the calorie consumption rate include body weight, fitness training intensity, exercise level and physiological metabolism. Though the calorie consumption rate is not accurately calculated, but it can be estimated using conventional approximation methodology.

Incidentally, according to the inventive concept shown in FIG. 1, for the processing of the physical activity signal, the exemplary embodiment of the present invention can also provide another judgment mechanism for determining whether or not the pre-processed displacement signal Ds1 of the feature point is being mixed with the pending physiological signal in the signal mixing process (S240) for noise elimination before calculating the information $D_2$ of physical activity by using the pre-processed displacement signal Ds.

Figure 8:
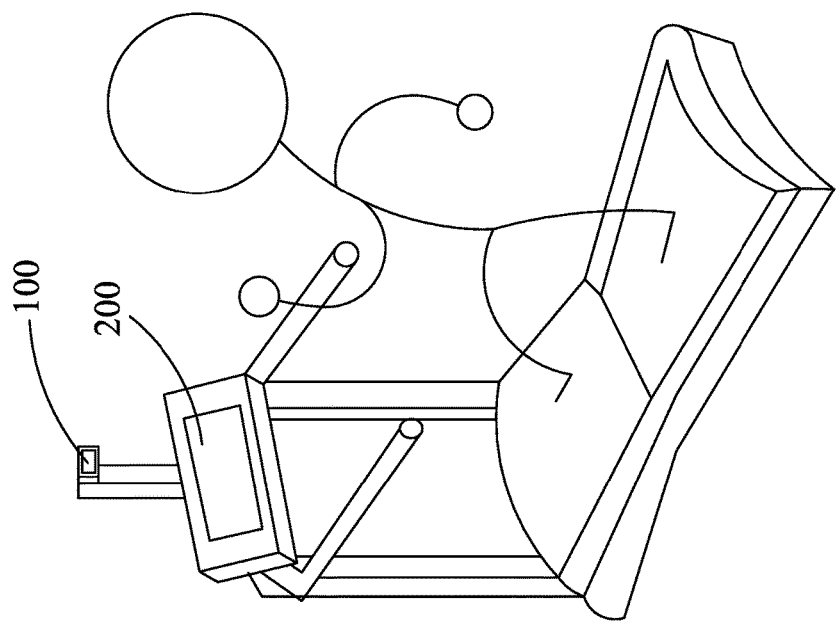
FIG. 8 is a schematic view showing scenario physical settings for exerciser acting on a treadmill in an exemplary embodiment of the present invention.

FIG. 8 is a schematic view showing scenario physical settings for exerciser acting on a treadmill in an exemplary embodiment of the present invention, wherein the detecting unit of image sensor 100 and processing unit of signal processing system 200 are placed in front of the treadmill respectively. The present embodiment is capable of simultaneously measuring the physiological information and the information of the physical activity in a contactless method, wherein the physiological information includes heart rhythm value, pulse rate, and exercise intensity calculated by using the heart rhythm value; and the information of the physical activity includes step count, jogging speed, calorie consumption, exercise duration and distance. Moreover, it is possible to simultaneously monitor both of the physiological state and physical activity state by providing only an image sensor 100 and a contactless signal processing system 200 described above. This method eliminates the inconvenience of wearing redundant cumbersome accessories such that it not only can carry out a variety of information analysis and operation, but also can provide users for monitoring physiological signals and physical activity signal in a comfortable environment without wearing any device. Additionally, the method can accurately measure the heart rhythm signal with elimination of the motion noise even in the case of human movement, which means that it can solve the pending problem for inaccuracy in contactless detection of heart rhythm signal, which is incurred by the heart rhythm signal being susceptible to movement of the user's face.

The foregoing descriptions of the preferred embodiments of the present invention have been presented for purposes of illustration and explanations. It is not intended to be exclusive or to limit the invention to the precise form or to the disclosed exemplary embodiments. Accordingly, the foregoing description should be regarded as illustrative rather than restrictive. Obviously, many modifications and variations will be apparent to practitioners skilled in this art. The embodiments are chosen and described in order to best explain the principles of the invention and its best mode for practical applications, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like is not necessary to confine the scope defined by the claims to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules on the requirement of an abstract for the purpose of conducting a survey on patent documents, and should not be used to interpret or limit the scope or meaning of the claims. Any advantages and benefits described hereto may not apply to all embodiments of the invention. It should be appreciated that variations may be made in the embodiments described by persons skilled in the art without departing from the scope of the present invention as defined by the following claims. Moreover, no element and component in the present disclosure are intended to be dedicated to the public regardless of whether the element or component is explicitly recited in the following claims.

What is claimed is:

1. A contactless detection method with noise elimination for information of physiological and physical activities, comprising steps of:
   providing an image sensor for capturing an image of a human body portion to produce a primitive image;
   defining a feature point of the human body portion from the primitive image;
   tracing an information for coordinate movement of the feature point to create a displacement signal;
   capturing a complexion fluctuation of the human body portion to form a pending physiological signal including a noise;
   inputting the displacement signal and the pending physiological signal into an adaptive filter to eliminate the noise in the pending physiological signal for generating an ideal physiological signal;
   performing a first peak/trough detection on the ideal physiological signal to calculate out an physiological information; and
   performing a second peak/trough detection on the displacement signal to calculate out an information of physical activity.

2. The contactless detection method with noise elimination for information of physiological and physical activities as described in claim 1, further comprising:
   defining a region of interest for the human body portion in the primitive image; and
   updating the coordinate of the region of interest dynamically in accordance with the displacement signal while the region of interest moving with the human body portion.

3. The contactless detection method with noise elimination for information of physiological and physical activities as described in claim 2, wherein the pending physiological signal is a pending heart rhythm signal, the ideal physiological signal is an ideal heart rhythm signal, and the physiological information is a value of heart rhythm, the method further comprising:
   extracting a green channel signal, a red channel signal and a blue channel signal from the region of interest; and
   performing a color space linear combination algorithm on the red channel signal, the green channel signal, and the blue channel signal prior to inputting the pending heart rhythm signal to the adaptive filter.

4. The contactless detection method with noise elimination for information of physiological and physical activities as described in claim 3, further comprising:
   locking a relative positional relationship between the feature point and the region of interest for defining the feature point and the region of interest.

5. The contactless detection method with noise elimination for information of physiological and physical activities as described in claim 3, further comprising:
   tracing an information for coordinate movement of a center point in the region of interest for replacing the information for the coordinate movement of the feature point to create another displacement signal.

6. The contactless detection method with noise elimination for information of physiological and physical activities as described in claim 3, further comprising:
   performing a band pass filtering and a direct-current subtraction on the displacement signal to generate a pre-processed displacement signal prior to inputting the displacement signal into the adaptive filter and performing the second peak/trough detection on the displacement signal.

7. The contactless detection method with noise elimination for information of physiological and physical activities as described in claim 6, further comprising:
   performing another band pass filtering on the ideal heart rhythm signal prior to performing the first peak/trough detection.

8. The contactless detection method with noise elimination for information of physiological and physical activities as described in claim 6, further comprising:
   performing a temporal normalization to enhance a signal-to-noise ratio on the ideal heart rhythm signal prior to performing the first peak/trough detection.

9. The contactless detection method with noise elimination for information of physiological and physical activities as described in claim 6, wherein the procedure of generating the ideal heart rhythm signal comprising:
   taking the pre-processed displacement signal as a reference offset source signal for the adaptive filter;
   offering a filter coefficient for operation with the reference offset source signal to obtain a hypothetical noise approaching the noise; and
   performing a SUM logical operation on both of the hypothetical noise and the pending heart rhythm signal to obtain the ideal heart rhythm signal.

10. The contactless detection method with noise elimination for information of physiological and physical activities as described in claim 6, further comprising:
    providing a peak/trough detection algorithm;
    judging whether or not the pre-processed displacement signal has an amplitude below a threshold value; and
    if the amplitude of the pre-processed displacement signal is below the threshold value, a corresponding pulse rate is detected with the peak/trough detection algorithm from a time domain waveform of the ideal heart rhythm signal; otherwise, an instant pulse rate is measured by detecting a maximum occurrence within a normal heartbeat range in a frequency domain spectrum of the ideal heart rhythm signal.

11. The contactless detection method with noise elimination for information of physiological and physical activities as described in claim 6, further comprising:
    providing a first judging mechanism comprising steps of:
    judging the human body portion is in active condition or at rest condition;
    if the human body portion is judged as in active condition, the pending physiological signal and the pre-processed displacement signal will be input into the adaptive filter for being treated by a signal mixing process to eliminate the noise; and
    if the human body portion is judged as at rest condition, the pending physiological signal will not be input into the adaptive filter for being treated by the signal mixing process so that the pending physiological signal is directly used to calculate the physiological information; and providing a second judging mechanism for determining whether or not the pre-processed displacement signal of the feature point is being mixed with the pending physiological signal in the signal mixing process before calculating the information of physical activity by using the pre-processed displacement signal.

12. The contactless detection method with noise elimination for information of physiological and physical activities as described in claim 1, wherein the information of the physical activity is selected from a group consisting of step count, jogging speed, calorie consumption, exercise duration and distance.

13. The contactless detection method with noise elimination for information of physiological and physical activities as described in claim 1, wherein the adaptive filter is selected from a group consisting of single stage adaptive filter and cascade adaptive filter.

\* \* \* \* \*